United States Patent [19]

Enomoto et al.

[11] 4,296,233

[45] Oct. 20, 1981

[54] CONJUGATE OF AMINO SUGAR-STEROID HORMONE

[75] Inventors: Satoru Enomoto, Fujisawa; Kiro Asano, Kukizaki; Hiromitsu Tanaka, Tokyo, all of Japan

[73] Assignee: Kureha Kagaku Kogyo Kabushiki Kaisha, Tokyo, Japan

[21] Appl. No.: 25,073

[22] Filed: Mar. 29, 1979

[30] Foreign Application Priority Data

Apr. 14, 1978 [JP] Japan ................................. 53-44034

[51] Int. Cl.³ .............................................. C07J 17/00
[52] U.S. Cl. .......................................... 536/5; 435/7; 424/12
[58] Field of Search ..................... 536/5, 6, 7; 424/182

[56] References Cited

U.S. PATENT DOCUMENTS

| | | | |
|---|---|---|---|
| 3,427,300 | 2/1969 | Sarett et al. | 536/5 |
| 3,678,029 | 7/1972 | Joseph et al. | 536/5 |
| 3,836,520 | 9/1974 | Stache et al. | 536/7 |
| 3,963,697 | 6/1976 | Coombes | 536/7 |
| 4,003,998 | 1/1977 | Lösel et al. | 536/7 |
| 4,021,535 | 5/1977 | Polito | 536/7 |
| 4,088,757 | 5/1978 | Petersen | 536/5 |

Primary Examiner—Johnnie R. Brown
Attorney, Agent, or Firm—Oblon, Fisher, Spivak, McClelland & Maier

[57] ABSTRACT

Conjugates of amino sugar-steroid hormone are prepared by binding an amino sugar to steroid hormone at 3- or 17-position by a direct reaction or by binding with a binding agent, and the conjugate is useful in an enzyme immunoassay method.

5 Claims, 1 Drawing Figure

CONJUGATE OF AMINO SUGAR-STEROID HORMONE

BACKGROUND OF THE INVENTION

1. Field of the Invention

The present invention relates to novel conjugates of amino sugar-steroid hormone.

2. Description of the Prior Art

An enzyme immunoassay method for determining activity of an enzyme bound to a physiologically active substance has been proposed as one of effective quantitative methods for determining a small amount of an insoluble physiologically active substance such as steroid hormones which contain only quite small amount in a biological body in Japanese Unexamined Patent Publication No. 10550/1972.

When the enzyme immunoassay method is applied for determining a steroid hormone one of important physiologically active substances, the steroid hormone is not soluble in water and a preparation of a complex of the steroid hormone and enzyme should be carried out in an organic solvent whereby certain troubles such as denaturation of enzyme by the organic solvent have been caused.

Thus, in order to increase water solubility of the steroid hormone without damage of its physiological activity, various methods have been proposed. However, any effective technology has not been proposed.

SUMMARY OF THE INVENTION

It is an object of the present invention to provide novel conjugates of amino sugar-steroid hormone which are useful for various physiological activities.

It is another object of the present invention to provide novel conjugates of amino sugar-steroid hormone which are used for enzyme immunoassay methods.

The foregoing and other objects of the present invention have been attained by providing novel conjugates of amino sugar-steroid hormone obtained by binding carboxyl group of an amino sugar to a steroid hormone at 3- or 17-position by a direct reaction or by binding with a binding agent.

DETAILED DESCRIPTION OF THE PREFERRED EMBODIMENTS

Figure 1:
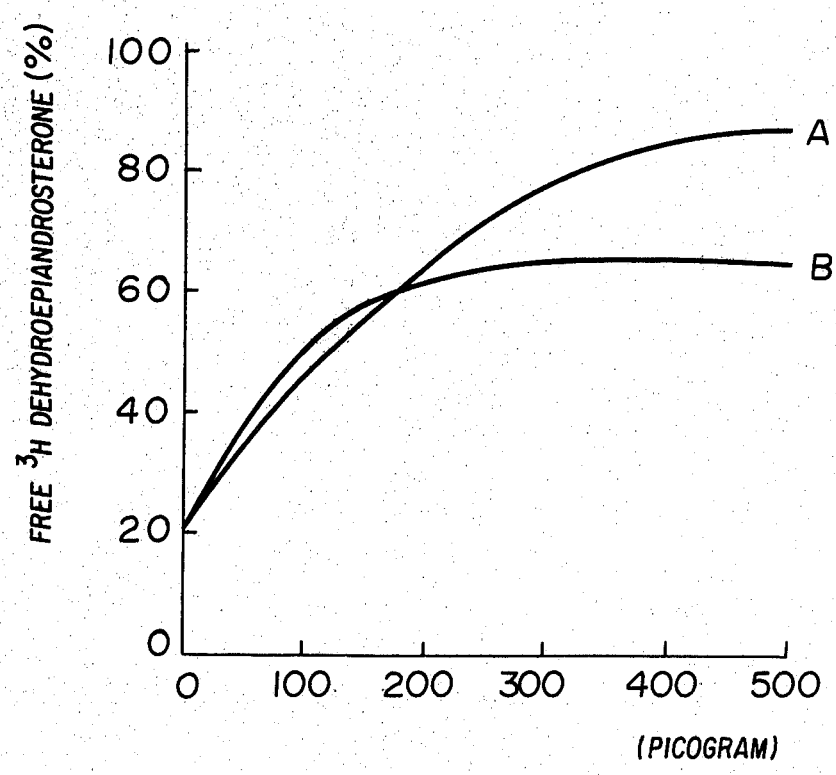

The preparations, properties and usages of the novel conjugates of amino sugar-steroid hormone will be illustrated in detail.

Steroid Hormones

The steroid hormones used in the present invention include various steroid hormones in biological bodies and synthetic steroid hormones.

Suitable steroid hormones include male hormones such as 17β-hydroxy-4-androsten-3-one(testosterone); and 3β-hydroxy-5-androsten-17-one(dehydroepiandrosterone) female hormones such as 1,3,5(10)-estratriene-3,17β-diol(estradiol); 5β-pregnane-3α, 20α-diol(-pregnanediol); luteinizing hormones such as 4-pregnene-3,20-dione, adrenocorticol hormones such as 11β,17α,21-trihydroxy-4-pregnene-3,20-dione; and 11β,21-dihydroxy-4-pregnene-3,20-dione.

Suitable synthetic steroid hormones include carbohydrate adrenocorticol hormones such as prednisone; and desoxymethasone, anabolic steroids such as mestanolone and androstanolone; cholesterol desorbers such as ursodesoxycholic acid; and methandienone; and cholesterol absorbers such as β-sitosterol and Alphaxalone.

Amino sugars

Suitable amino sugars having carboxyl group used in the present invention include 2-amino-2-deoxy-glucuronic acid; 2-amino-2-deoxy-3-O-(1-carboxyethyl)-D-glucose and 2-amino-2-deoxy-3-O-β-D-glucopyranurosyl-D-galactose (chondrosine).

The amino sugars to which carboxyl group can be easily introduced, include 2-amino-2-deoxy-glucose and 2-amino-2-deoxy-4-O-α-D-glucopyranosyl-α-D-glucopyranose.

The conjugates of amino sugar-steroid hormone can be produced as follows.

Conjugates can be produced with the amino sugar and the steroid hormone compound by their direct reaction or by using a suitable binding agent between them.

The binding agent can be a compound having the formula

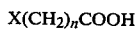
$$X(CH_2)_nCOOH$$

(n is 1 or 2; and X is a halogen atom) such as α-monochloroacetic acid, α-monobromoacetic acid, and β-monobromopropionic acid; a compound having the formula

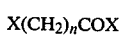
$$X(CH_2)_nCOX$$

such as α-monochloroacetyl chloride and α-monobromoacetylbromide; a compound having the formula

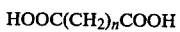
$$HOOC(CH_2)_nCOOH$$

or

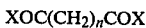
$$XOC(CH_2)_nCOX$$

such as malonic acid and succinic acid and acid dichloride or dibromide thereof.

These binding agent can be used by the conventional chemical manner.

The conjugates can be produced by reacting a steroid hormone, a steroid hormone derivative having a binding group with an amino sugar or a salt thereof.

The steroid hormone derivative having a binding group can be easily obtained by reacting a steroid hormone with the above-mentioned binding agent.

The binding agent should be reacted with a functional group such as OH group at 3- or 17-position of the selected steroid hormone. When the selected steroid hormone has not OH group, at 3- or 17-position, the functional group is converted to OH group before the reaction.

The reaction of the steroid hormone with the binding agent is preferably carried out in a solvent such as anhydrous tetrahydrofuran preferably an aprotic solvent. The reaction temperature is usually not so high and sometimes, room temperature or lower.

The amino sugar is usually used in a form of a salt thereof especially a silver salt.

It is possible to modify the amino sugar before reacting with the steroid hormone or its derivative.

The reaction of a metal salt of amino sugar with the steroid hormone derivative can be carried out by mixing them in solvent such as DMSO in the dark.

The reaction temperature can be about room temperature though it can be varied.

The resulting product can be purified by elution column chromatography on silica gel with a buffer solution.

The present invention will be further illustrated by certain examples and references which are provided for purposes of illustration only and are not intended to be limiting the present invention.

EXAMPLE 1

A conjugate of 3β-hydroxy-5-androsten-17-one(-dehydroepiandrosterone) at 3-position and 2-amino-2-deoxy-3-O-β-glucopyranurosyl-D-galactose (chondrosine) at 6-position with a binding agent of bromoacetyl bromide.

(1) Preparation of 3β-bromoacetyl-5-androsten-17-one 5.0080 Grams of 3β-hydroxy-5-androsten-17-one was dissolved in 350 ml of CCl$_4$ and 1.3705 g of pyridine was added to the solution.

A solution prepared by dissolving 11.65 g of bromoacetyl bromide in CCl$_4$ was added dropwise to the former solution with stirring at room temperature to react them for about 2 hours. After the reaction, the reaction mixture was filtered and a filtrate was concentrated and dried. The residual solid of 3β-bromoacetyl-5-androsten-17-one was dissolved in methanol and recrystallized to obtain 7.11 g (Yield 93.30%) of the compound (1) having a melting point of 150° C.

(2) Preparation of silver salt of chondrosine 1.6 Grams of chondrosine was dissolved in 100 cc of water and equal mole of KOH was added and the reaction mixture was dried by a lyophilization to obtain potassium salt of chondrosine at substantially stoichiometrical ratio.

1.5 Grams of potassium salt of chondrosine was dissolved in 15 ml of water and then, 60 ml of methanol was added. A solution prepared by dissolving 0.7786 g of AgNO$_3$ in a small amount of water was added to the former solution. The precipitate was separated by a filtration and washed with methanol and then, with ether and dried to obtain 1.495 g of silver salt of chondrosine.

(3) 1.133 Grams (0.00245 mole) of silver salt of chondrosine was dissolved in 70 ml of DMSO (dimethylsulfoxide) and 0.84 g of the compound (1) was added to the solution to react them at room temperature for 2 days. After the reaction, AgBr was separated by a centrifugal separation and DMSO was distilled off from the resulting supernatant at 45° to 50° C. under a reduced pressure and then, 70 ml of ethanol was added to the residual solid and a floating insoluble material was separated and a filtrate was concentrated under a reduced pressure and poured into 2 ml of cold water to precipitate the product. The precipitate was dried and washed with ether and dried to obtain 0.36 g of a conjugate of chondrosine-dehydroepiandrosterone having the formula

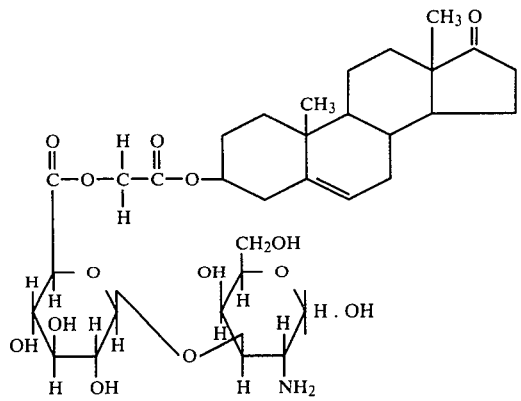

Physical properties

1. IR spectrum (cm$^{-1}$): 3400, 2930, 2900, 1738, 1615, 1465, 1450, 1435, 1400, 1382, 1372, 1290, 1210, 1138, 1090, 1058, 1023, 950, 880, 845, 830, 810, 798, 700, 600, 580

2. Elementary Analysis: C$_{33}$H$_{49}$NO$_{14}$: (Molecular weight 683)

| | C | H | N |
|---|---|---|---|
| Calculated (%) | 57.98 | 7.17 | 2.05 |
| Found (%) | 58.4 | 7.3 | 1.97 |

3. Solubility:

The conjugate is dissolved at $4.39 \times 10^{-5}$ mole/liter (30 mg/liter) in a mixed solvent of 98 vol.% of water and 2 vol.% of ethanol.

Solubility of dehydroepiandrosterone in the same mixed solvent measured by absorbance at 235 mμ is $0.24 \times 10^{-5}$ mole/liter.

The fact shows that the solubility of the conjugate is more than 18 times to that of the non-conjugate dehydroepiandrosterone.

EXAMPLE 2

A conjugate of 1,3,5(10)-estratriene-3,17β-diol (estradiol) and chondrosine at 17-position with a binding agent of bromoacetyl bromide.

(1) Preparation of 1,3,5(10)-estratriene-3-hydroxy-17β-bromoacetate

10 Grams of estradiol was dissolved in 400 ml of anhydrous THF(tetrahydrofuran) and 8.8 g of anhydrous pyridine was added to the solution and the mixture was cooled to −7° C. to −5° C. A solution prepared by dissolving 22.5 g of bromoacetyl bromide in 74 g of CCl$_4$ was added dropwise to the mixture and the reaction mixture was kept in one night. After the reaction, a precipitate was separated by a filtration and THF was distilled off from the filtrate and the residual solid was dissolved in ether and recrystallized to obtain 1,3,5(10)-estratriene-3,17β-bis(bromoacetate).

2 Grams of the product was dissolved in 900 ml of methanol. A solution prepared by dissolving 0.24 g of K$_2$CO$_3$ in 20 ml of water was added dropwise to the former solution at −5° C. After reacting them for 30 to 40 minutes, 1000 ml of water was added and the resulting precipitate was separated and dried. The product was identified to be the compound (1) by IR spectrum and elementary analysis.

(2) Preparation of conjugate 1.133 Grams of silver salt of chondrosine was dissolved in 70 ml of DMSO and 0.85 g of the compound (1) was added to react them at room temperature for 2 days. After the reaction, the precipitate was separated and DMSO was distilled off from the filtrate and 70 ml of ethanol was added to the residual solid. The insoluble material was separated and then, ethanol was distilled off from the filtrate and the residue was mixed with 20 ml of cold water to crystallize the product. The crystalline product was washed with ether and dried. The product was identified to be the conjugate having the following formula by IR spectrum, and elementary analysis (Yield 0.4 g).

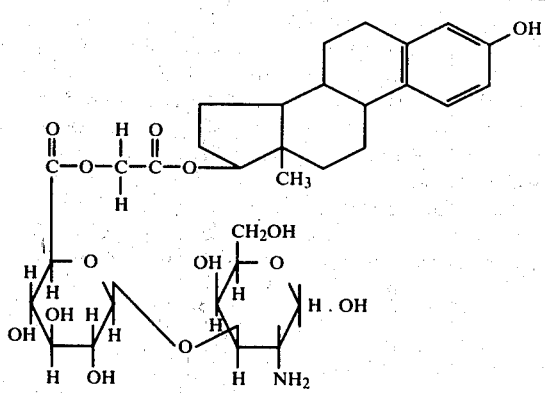

| Elementary analysis: $C_{32}H_{45}NO_{14}$ | | | |
| --- | --- | --- | --- |
| | C | H | N |
| Calculated (%) | 57.57 | 6.75 | 2.10 |
| Found (%) | 57.5 | 6.8 | 2.0 |

In accordance with the method of Example 1, a solubility of the product was measured. The solubility of the product was $6.5 \times 10^{-5}$ mole/liter which was about 20 times to that of estradiol.

EXAMPLE 3

Conjugate of dehydroepiandrosterone (hereinafter referring as to DHS) and chondrosine at 17-position with a binding agent of bromoacetyl bromide.

The group of $>C=O$ at 17-position of DHS was converted to $>C-OH$ with LiAlH$_4$ and bromoacetyl bromide was added and the reaction mixture was treated by the process of Example 2 to obtain the object conjugate.

Conversion to Hydroxyl group at 17-position 6.84 Grams of DHS was dissolved in 200 ml of anhydrous ether and 0.4 g of LiAlH$_4$ dispersed in 20 ml of anhydrous ether was added to the solution and the mixture was refluxed for 15 hours to react them. After the reaction, water was added to separate ether phase and ether was distilled off from the ether phase. The ketone group at 17-position was substantially and converted to hydroxyl group. The fact was easily found by elimination of absorption for ketone group (1720 cm$^{-1}$) in IR spectrum.

The conjugate has the formula

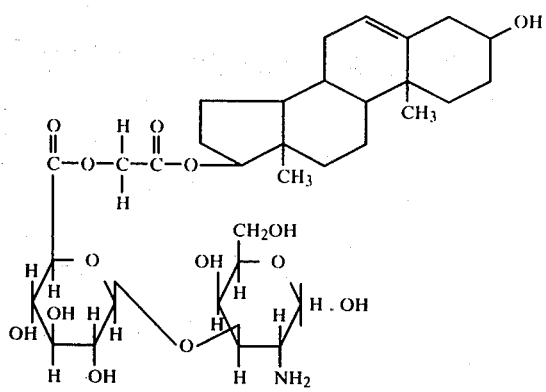

A solubility of the conjugate in water was substantially same with that of the conjugate at 3-position in Example 1.

EXAMPLE 4

Conjugate of DHS and 2-amino-2-deoxy-α-D-glucuronic acid.

The group of OH at 3-position of DHS was converted to Cl and the modified DHS was reacted with silver 2-amino-2-deoxy-α-D-glucuronate in dioxane.

(1) Chlorination of DHS

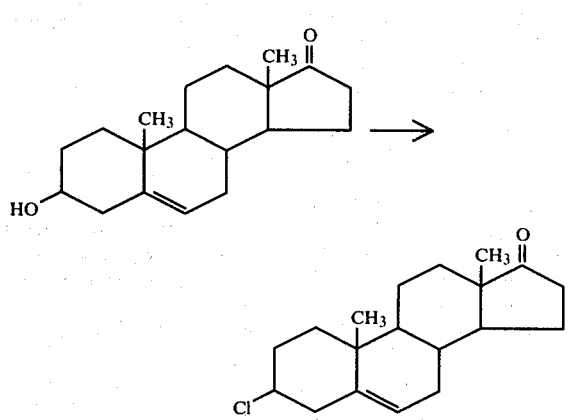

2 Grams of DHS was dissolved in 50 ml of chloroform and 2.74 g of CaCO$_3$ was added to the solution under cooling at 0° C. and then, 2.96 g of PCl$_5$ was added to react them for 3 hours. After the reaction, the reaction mixture was filtered and the filtrate was concentrated and dried and dissolved in petroleum ether. The unreacted DHS was insoluble and it was separated by a filtration. The filtrate was concentrated and dried and the residue was dissolved in a mixed solvent of benzene and pentane (1:2) and it was adsorbed in an Al$_2$O$_3$ column and then, it was eluted with ether and the solution was concentrated and dried to obtain a white solid.

| Elementary Analysis: $C_{19}H_{27}OCl$ (Molecular weight 306.5) | | | |
| --- | --- | --- | --- |
| | C | H | Cl |
| Calculated (%) | 74.39 | 8.81 | 11.58 |
| Found (%) | 74.0 | 8.8 | 12.1 |

(2) Preparation of silver 2-amino-2-deoxy-glucuronate 2.31 Grams of 2-amino-2-deoxy-glucuronic acid was dissolved in a solution of 0.85 g of KOH in 200 ml of water. A solution of 2.035 g of AgNO$_3$ in 100 ml of water was added to the former solution to precipitate the silver salt (Yield about 80%).

(3) Preparation of conjugate at 3-position

In accordance with the process of Example 1, the reaction of the compound (1) with the compound (2) was carried out to obtain a conjugate at 3-position having the formula

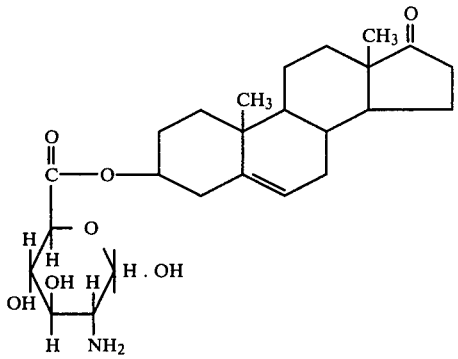

Elementary Analysis:

|  | C | H | N |
|---|---|---|---|
| Calculated (%) | 64.99 | 7.99 | 3.03 |
| Found (%) | 64.1 | 7.9 | 3.0 |

Solubility of the conjugate was $4.02 \times 10^{-5}$ mole/liter (Method of Example 1).

EXAMPLE 5

Reaction of enzyme with the conjugate of chondrosine-dehydroepiandrosterone.

In accordance with the method described in *Clin. Chem. Acta* Vol. 40, Page 187 (1972) by K. Miedema, J. Borlhowwer and J. Otten, the reaction was carried out.

7.5 Milligrams (enzyme activity 30 $\mu$/mg) of enzyme alkaliphosphatase (Type VII manufactured by Sigma Chem. Co. in U.S.A.)(hereinafter referring to as AP) and 1 mg of the conjugate of Example 1 (hereinafter referring to as C-D complex) were dissolved in 2 ml of 0.04 M phosphoric acid buffer solution (pH: 7.4) and 0.2 ml of 25% glutaraldehyde was added dropwise to the solution and the mixture was stirred for 6 hours. The supernatant separated by a centrifugal separation was chromatographed on a Sephadex G100 with a buffer solution (pH: 7.4) of 0.04 M-phosphoric acid to obtain the purified combined product.

In accordance with the method described in said document and Bunseki Library 3 Rinshokagakubunseki IV Koso (Analysis library 3 Clinical Chemical Analysis IV Enzyme) Page 96 to 100 (by Nippon Bunsekikagaku Kai: Published by Tokyo Kagaku Dojin in 1975), AP activity of the purified product was studied to find no deterioration of enzymic activity.

In order to confirm the presence of C-D complex combined to AP, the combined product was analyzed by a competitive immunoassay method described in Seikagaku Jikken Koza (Biochemical Experiment Hormones (First) Page 217 to 252 (by Nippon Seikagaku Kai) (published by Tokyo Kagaku Dojin in 1977).

Dehydroepiandrosterone labelled by tritium ($^3$H) was bound to the antibody which is active to the ketone group at 17-position of dehydroepiandrosterone. The combined product or dehydroepiandrosterone was added to the system of the antibody and the labelled compound to measure the amount of free $^3$H-dehydroepiandrosterone release from the system. The results are shown in FIG. 1.

In FIG. 1, the curve A shows relation of the amount of combined product to the free $^3$H-dehydroepiandrosterone and the curve B shows relation of the amount of dehydroepiandrosterone and to the free $^3$H-dehydroepiandrosterone.

In both cases, the amount of free $^3$H-dehydroepiandrosterone was increased by the addition of the combined product or dehydroepiandrosterone whereby the their binding to the antibody is found.

The advantage of the conjugate of the present invention is that the binding ability of the combined product to the antibody is higher than that of dehydroepiandrosterone at more than 200 pg though the molecular weight of the combined product is remarkably larger than that of dehydroepiandrosterone.

In this example, alkaliphosphatase was used. Thus, the similar effects can be obtained by using the other enzymes for immunoassay such as catalase, urease, peroxidase, and esterase.

When the present invention is applied for various steroid hormones, preferable pharmacological effects such as improvement of biological absorbability of hormones.

What is claimed is:

1. A conjugate of an amino sugar and a steroid hormone having the formula:

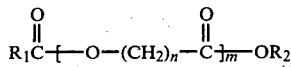

wherein $R_1C$ is a radical of a carboxyl group containing amino sugar selected from the group consisting of 2-amino-2-deoxy-glucuronic acid, 2-amino-2-deoxy-3-O-(1-carboxyethyl) D-glucose and 2-amino-2-deoxy-3-O-$\beta$-D-glucopyranurosyl-D-galactose; R$_2$ is a radical of a steroid hormone selected from the group consisting of 17$\beta$-hydroxy-4-androsten-3-one; 3$\beta$-hydroxy-5-androsten-17-one; 1,3,5 (10)-estratriene-3,17 $\beta$-diol; 5$\beta$-pregnane-3$\alpha$, 20$\alpha$-diol; 4-pregnene-3, 20-dione; 11$\beta$, 17$\alpha$, 21-trihydroxy-4-pregnene-3, 20-dione; 11$\beta$, 21-dihydroxy-4-pregnene-3,20-dione; prednisone; desoxymethasone, mestanolone; androstanolone; unsodeoxycholic acid methanedienome; $\beta$-sitosterol and Alphaxalone, the bonding between said amino sugar radical and said steroid hormone radical occurring only at the 3 or 17 position of said steroid radical; m is 0 or 1 and n is 1 or 2.

2. A process for producing the amino sugar-steroid hormone conjugate of claim 1, comprising: reacting a carboxyl group containing amino sugar with a steroid hormone, said reaction occurring between the carboxyl group of said amino sugar and the 3- or 17-position of said steroid hormone.

3. The process of claim 2, wherein said carboxyl group containing amino sugar is in the form of its silver salt.

4. A process for producing the amino sugar-steroid hormone conjugate of claim 1, comprising; reacting a carboxyl group containing amino sugar with said steroid hormone at the 3- or 17-position of said steroid hormone in the presence of a binding agent, said binding agent being selected from the group consisting of:

X(CH₂)ₙCOOH,

X(CH₂)ₙCOX,

HOOC(CH₂)ₙCOOH, and

XOC(CH₂)ₙCOX wherein n is 1 or 2 and X is a halogen atom.
5. The process of claim 4, wherein said conjugate is acetylized.

* * * * *